United States Patent

Sebag et al.

[11] 4,290,956
[45] Sep. 22, 1981

[54] TENSIO-ACTIVE POLYPOD COMPOUNDS, PROCESS FOR PREPARING THEM AND COMPOSITIONS CONTAINING THEM

[75] Inventors: Henri Sebag, Paris; Guy Vanlerberghe, Claye-Souilly, both of France

[73] Assignee: L'Oreal, Paris, France

[21] Appl. No.: 56,204

[22] Filed: Jul. 10, 1979

[30] Foreign Application Priority Data

Jul. 13, 1978 [FR] France ................... 78 21081

[51] Int. Cl.$^3$ .................................. C07D 323/00
[52] U.S. Cl. ...................................... 260/338
[58] Field of Search .............................. 260/338

[56] References Cited

U.S. PATENT DOCUMENTS

| | | | |
|---|---|---|---|
| 3,297,635 | 1/1967 | Bergman et al. | 260/338 |
| 3,534,064 | 10/1970 | Dietrich et al. | 260/338 |
| 3,840,606 | 10/1974 | Vanlerberghe | 568/623 |
| 3,959,390 | 5/1976 | Vanlerberghe | 568/623 |
| 4,025,523 | 5/1977 | Steiner et al. | 260/338 X |
| 4,138,427 | 2/1979 | Vanlerberghe et al. | 260/459 A |

FOREIGN PATENT DOCUMENTS 2027585 10/1970 France .

OTHER PUBLICATIONS

Chem. Abstracts 69:36676.

*Primary Examiner*—Ethel G. Love
*Attorney, Agent, or Firm*—Fleit & Jacobson

[57] ABSTRACT

Tensio-active cyclic polyethers of the general formula:

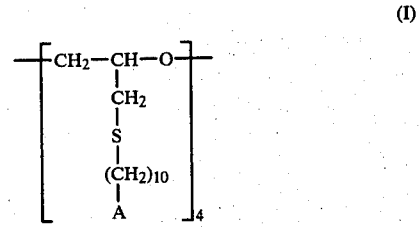

where A refers to a hydrophile block chosen from the amine, ammonium, ammonio alkyl carboxylate, ammonio alkyl sulfonate, amide, sulfonamide, ether, thioether, hydroxyl, ester and acid groupings.

These polyethers may be prepared (1) by reaction of alcohol or of undecylenic acid with thioacetic acid, (2) saponification with an alkaline base, (3) reaction of the product obtained in (2) with the tetramer of epichlorohydrin or of epibromohydrin, (4) reaction of mesylate or tosylate of the compound obtained in (3) either (a) with dimethylamine or methylethanolamine, the resulting compound being able to be salified or alkylated, or (b) with the mercapto ethanol or mercapto glycerol; the compounds thereby obtained being then able to be submitted to reactions of polyaddition of ethylene oxide and/or of glycidol oxide.

These tensio-active cyclic polyethers are suitable for use in the cosmetic, textile, insecticide and similar industries.

28 Claims, No Drawings

TENSIO-ACTIVE POLYPOD COMPOUNDS, PROCESS FOR PREPARING THEM AND COMPOSITIONS CONTAINING THEM

The invention relates to new tensio-active cyclic polyethers, called "Polypods", the processes for preparing same and the compositions containing same.

The new tensio-active cyclic polyethers possess remarkable characteristics which set them apart from similar compounds previously described. By their chemical structure, they are somewhat similar to Crown ethers, which have been very much studied these last few years as complexing agents of cations of alkaline metals or alkaline earth metals.

They are different in regard to their amphiphile character, i.e., an affinity at the same time for water and for organic media, which gives them a strong interfacial activity.

They are also distinguished from conventional surface-active agents, which include a single lipophile chain per molecule.

As is well known, the latter, when they are dissolved in water, show—beyond a threshold of concentration called critical micellar concentration—a body of properties which are very advantageous for a large number of applications. In particular, at concentrations at least equal to this threshold, they dissolve in water organic substances, such as liposoluble dyes and hydrocarbides.

The compounds according to the invention possess dissolving properties at very weak concentrations, often quite a bit lower than the critical micellar concentration of surface-active agents which have one lipophile chain of comparable length.

This is an important advantage for certain uses of tensio-actives, such as, e.g., in pharmaceutical or cosmetic compositions, where there is an interest in reducing as much as possible the quantity of tensio-active compound used in order to not interfere with the active principle of these compositions.

In addition, the compounds of the invention are less aggressive to skin and to mucous membranes, especially to ocular membranes, or less "denaturing" to proteins, than the surface-active agents having one single lipophile chain per molecule and comparable functional groupings.

The new tensio-active cyclic polyethers, called "Polypods", may be represented by the general formula:

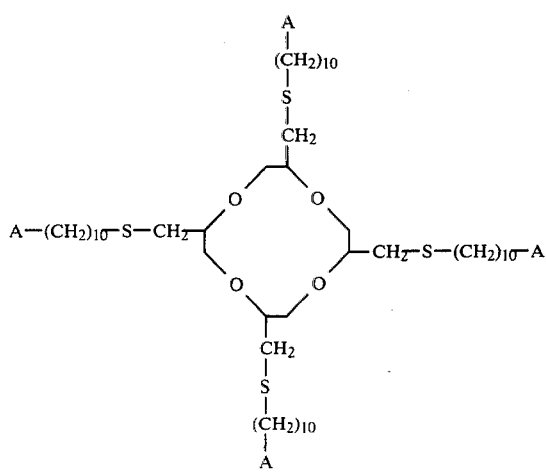

This general formula may also be written in a simplified form:

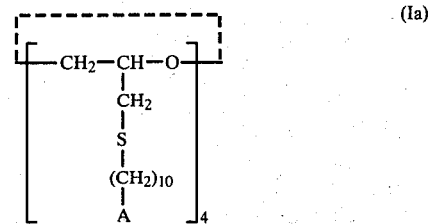

In formulas (I) and (Ia), A refers to a hydrophile block which is linked to the cycle by the thia-11 dodecamethylene radical which composes the lipophile ensemble.

The molecular configuration of the compounds of the invention resembles the form of certain invertebrates possessing several tentacles, whence the name of "Polypods" used here in order to refer to them, which has been proposed for similar compounds by R. Fornasier & F. Montanari, "Tetrahydronic Letters", No. 17, pp. 1381–1384 (1976).

The hydrophile block A, may be cationic, zwitterionic, anionic or non-ionic. It may contain one or several identical or different groupings, selected from the group consisting of amine, ammonium, ammonio alkyl carboxylate, ammonio alkyl sulfonate, amide, sulfonamide, ether, thioether, hydroxyl, ester and acid groupings.

The ionic or non-ionic hydrophil block A, may be chosen from one of the following groups:

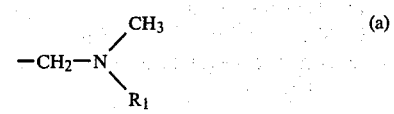

where
$R_1$ refers to $CH_3$ or $-\!\!+\!CH_2-CH_2-O\!+_{\!\!n}\!H$,
n refers to a whole or decimal number from 1 to 10;

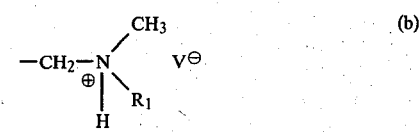

where
$V^{\ominus}$ refers to the anion of an organic or mineral acid and preferably a chloride, bromide, sulfate, phosphate, acetate, glycolate, lactate, tartrate, methane sulfonate, or paratoluene sulfonate anion,
$R_1$ has the meaning indicated in (a);

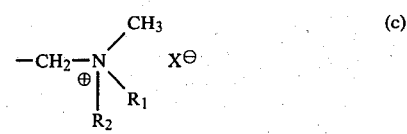

where
$R_2$ refers to an alkyl or hydroxyalkyl radical having from 1 to 3 carbon atoms and preferably a methyl, hydroxyethyl or dihydroxypropyl radical, $X^\ominus$ refers to an anion and preferably a chloride, bromide, iodide, methyl sulfate, mesylate or tosylate anion, $R_1$ has the meaning indicated in (a);

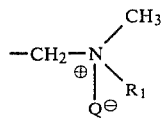 (d)

where $Q^\ominus$ refers to one of the groupings
—$CH_2COO^\ominus$
—$CH_2$—$CH_2COO^\ominus$
—$CH_2$—$CH_2$—$CH_2$—$SO_3^\ominus$, $R_1$ has the meaning indicated in (a);

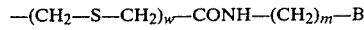 (e)

where m refers to the number 2 or 3,
w refers to the number 0 or 1,
B refers to one of the groupings:

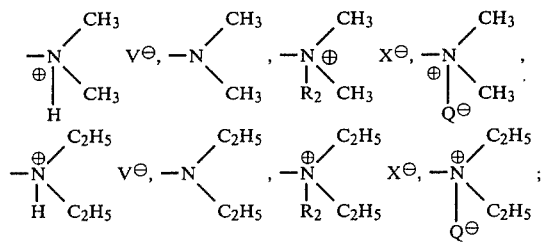

$Q^\ominus$ has the meaning indicated in (d),
$R_2$ and $X^\ominus$ have the meaning indicated in (c),
$V^\ominus$ has the meaning indicated in (b);

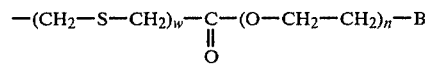 (f)

n having the meaning indicated in (a),
w refers to the number 0 and 1,
B having the meanings indicated in (e);

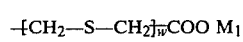 (g)

$M_1$ refers to an ammonium or an alkaline metal, such as lithium, sodium or potassium,
w refers to the number 0 or 1;

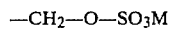 (h)

M refers to a hydrogen atom, ammonium or an alkali metal such as lithium, sodium or potassium;

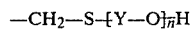 (i)

Y refers to the ethylene or hydroxypropylene radical,
n refers to a whole or decimal number from 1 to 10;

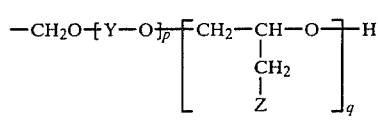 (j)

p and q, identical or different, refer to a whole or decimal number from 1 to 10, however, p and q do not refer simultaneously to zero, Y has the meaning shown in (i), Z may refer to one of the following groupings:

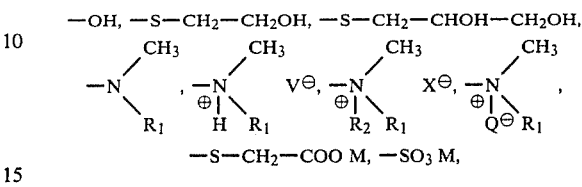

where $R_1$ has the meaning shown in (a),
$V^\ominus$ has the meaning shown in (b),
$R_2$ and $X^\ominus$ have the meaning shown in (c),
$Q^\ominus$ has the meaning shown in (d), M has the meaning shown in (h), and, in addition, when p refers to zero or when Y refers to the ethylene grouping, Z may refer to one of the groupings: —O—$SO_3M$ or —OCO—$CH_2$—$SO_3M$, M having the above meaning.

The distribution of the units:

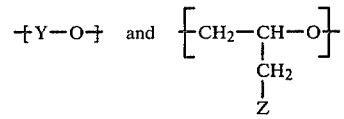

is most generally a distribution in blocks, as shown in formula (j). However, when Y refers to the hydroxypropylene grouping, the distribution may also be statistical.

The compounds of formula (I) may be prepared from undecylenic alcohol or undecylenic acid.

By reaction of these compounds with thioacetic acid followed by saponification with an alkaline base and preferably with sodium hydroxide or potassium hydroxide, one obtains, respectively:

mercapto-11 undecanol-1 of the formula

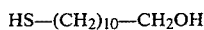 (II)

or mercapto-11 undecanoic-1 acid of the formula

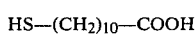 (III)

The preparation of these intermediary compounds of formulas (II) and (III) is described more in detail in Examples 1 and 2.

By reacting mercapto-11 undecanol-1 with the tetramer of epichlorohydrin or of epibromohydrin of formula (IV)

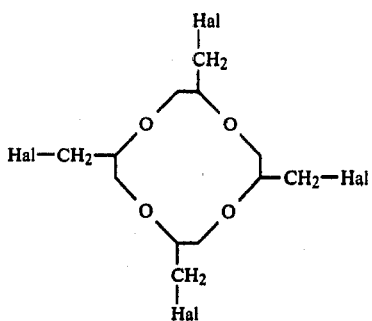

which, in simplified form, is written:

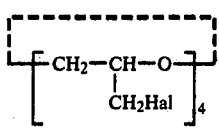

where Hal refers to chloride or bromide, one obtains the intermediary compound of formula (V)

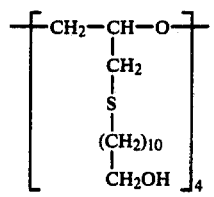

whose preparation is described in more detail in following Example 4.

Through reaction, either of mercapto-11 undecanoic-1 acid, or of its methylic or ethylic ester with the tetramer of epichlorohydrin or of epibromohydrin of formula (IV), or of methyl thioglycolate or of ethyl thioglycolate with the halogenated derivative, mesylate or tosylate of the compound of formula (V), one obtains the intermediary compound (VI):

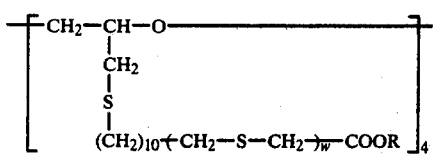

where R refers to hydrogen, $CH_3$ or $C_2H_5$, w refers to the number 0 or 1.

The invention also relates to the intermediary compounds of formula (VII):

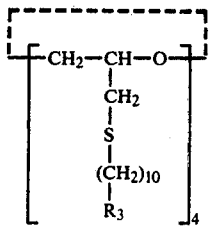

where $R_3$ refers to: $-CH_2OH$, $-CH_2-O-SO_2-CH_3$, $-CH_2-O-SO_2-C_6H_4-CH_3$, $-COOH$, $-COOCH_3$, $-COOC_2H_5$, $-CH_2-S-CH_2-COOH$, $-CH_2-S-CH_2-COOCH_3$ or $-CH_2-S-CH_2-COOC_2H_5$.

The tetramer of epichlorohydrin or of epibromohydrin of formula (IV) is prepared by polymerization of epichlorohydrin or of epibromohydrin in the presence of a Lewis acid catalyst, such as $BF_3$, $SnCl_4$, $SbCl_5$ or their mixture and purified by fractionation under reduced pressure. This process is described in Example 3.

The compounds of type I(a), responding to formula (I) in which A refers to grouping (a), are prepared by the reaction of dimethylamine or methylethanolamine, either with the chlorinated or brominated derivative of the intermediary compound of formula (V) (obtained by reacting the compound of formula (V) with, respectively, chloride of thionyl or hydrobromic acid), or with the mesylate or tosylate of this compound of formula (V).

The condensation of the amine may be carried out at atmospheric pressure or in an autoclave, at a temperature between 20° and 160° C. When one uses methylethanolamine, the compound obtained may possibly be oxyethylenated with ethylene oxide, and preferably with 1 to 10 moles ethylene oxide by mole of compound (I).

The compounds of type I(b), responding to formula (I) in which A refers to grouping (b), are derived from compounds I(a) by salification with a mineral or organic acid, and advantageously with one of the following acids: hydrochloric, hydrobromic, sulfuric, phosphoric, acetic, glycolic, lactic, tartaric, methane sulfonic, paratoluene sulfonic.

The compounds of type I(c), responding to formula (I) in which A refers to the grouping (c), may be prepared by the alkylation of compounds I(a) with an alkylating agent, such as chloride, bromide, iodide, mesylate or tosylate of methyl, dimethyl sulfate, glycol chlorohydrin or glycerol chlorohydrin.

The compounds of type I(c), in which $X^\ominus$ refers to a mesylate anion (methane sulfonate) or tosylate (p-toluene sulfonate), may also be obtained by the reaction of mesylate or tosylate of the intermediary compound of formula (V) with an amine of the formula:

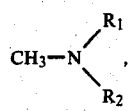

where
$R_1$ refers to $CH_3$ or $-[CH_2-CH_2-O]_{\overline{n}}H$,
n refers to a whole or decimal number from 1 to 10,
$R_2$ refers to a methyl radical, hydroxyethyl or dihydroxypropyl radical at a temperature of from 20° to 100° C.

The compounds of type I(d), responding to formula (I) in which A refers to the grouping (d), may be prepared by the alkylation of compounds I(a) with chloroacetate or chloropropionate of sodium or propane sultone, at a temperature of from 10° to 100° C.

The compounds of the type I(e), responding to formula (I) in which A refers to the grouping (e), may be prepared by the condensation of the intermediary compound of formula (VI) with a primary-tertiary diamine, such as dimethylamino ethylamine or dimethylamino propylamine.

The condensation of primary-tertiary diamine is carried out at a temperature of from 20° to 160° C.

The amine groupings of the amino amides thus obtained may then be combined in a salt with a mineral or organic acid as indicated for compounds of type I(b). They may also be alkylated with alkylating agents, such as those indicated for compounds of type I(c) and I(d).

The compounds of type I(f), responding to formula (I) in which A refers to grouping (f), are obtained by the condensation of the intermediary compound of formula (VI) with an oxyethylenated dimethylamine of the formula

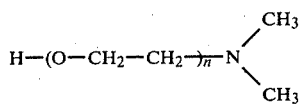

where n refers to a whole or decimal number from 1 to 10; the condensation is carried out at a temperature of from 20° to 160° C.; the amine groupings may then be combined in a salt with a mineral or organic acid or alkylated with an alkylating agent.

Compounds of the type I(g), responding to formula (I) in which A refers to grouping (g), are obtained by saponification of the methylic or ethylic ester of the intermediary compound of formula (VI), followed by neutralization with an alkaline or ammoniac hydroxide or, when w refers to zero, directly by reaction at a temperature of from 60° to 130° C. of the epichlorohydrin or epibromohydrin tetramer with the mercapto-11, undecanoic-1 acid in the presence of sodium or potassium methylate or ethylate, followed by neutralization with an alkaline hydroxide or ammoniac hydroxide.

The compounds of type I(h), responding to formula (I) in which A refers to the grouping (h), are obtained by sulfating of the intermediary compound of formula (V) with sulfuric chlorohydrin at a temperature of from 0° to 80° C. and possible neutralization with an alkaline or ammoniac hydroxide.

These reactions may be carried out without a solvent or in the presence of a solvent, such as chloroform, benzene, toluene, ether, glycol ethers.

The compounds of type I(i), responding to formula (I) in which A refers to grouping (i), are obtained by reaction of mercapto-ethanol or of mercaptoglycerol with mesylate or tosylate of the intermediary compound of formula (V) or with a halogenated compound derived from that one. These reactions are generally carried out in a solvent (preferably ethanol, propanol, isopropanol, t-butanol, butanol-1, glycols or monoethers of glycol, with possibly water) in the presence of methylate or ethylate or sodium or potassium, or sodium or potassium hydroxide, at temperatures between 60° and 160° C.

The derivatives thereby obtained may then initiate reactions of polyaddition of ethylene oxide and/or glycidol at 120° to 180° C. in the presence of an alkaline catalyst, advantageously in the presence of methylate or ethylate of sodium or of potassium. Advantageously they may be condensed with 1 to 10 moles of ethylene oxide and/or glycidol. In the case of addition at the same time of ethylene and of glycidol, these additions are generally carried out in two successive stages, the order of the additions being of no importance. These additions may be carried out with or without solvent.

The preferred solvents are: water, isopropanol, tertiobutanol, methyl ethyl ketone, methyl isobutyl ketone.

The compounds of the type I(j), responding to the formula (I) in which A refers to the grouping (j), are obtained, in one or several stages, by polyaddition of epoxydes with the intermediary compound of formula (V).

Useful epoxides are ethylene oxide, tertiobutyl glycidylether (TBGE), an epihalohydrin, such as epichlorohydrin or epibromohydrin, and their mixtures.

The reactions of polyaddition are generally sequential operations but, in the case where one uses TBGE and an epihalohydrin, one may also add the two reagents simultaneously or in a mixture.

In the case of addition of TBGE to the intermediary compound of formula (V), the protector tertio-butoxy groupings may be replaced by hydroxyl groupings by heating at 50° to 120° C. in the presence of a sulfocarboxylic or sulfonic acid. This reaction is described more in detail in French Pat. No. 2,027,585 and U.S. Pat. Nos. 3,840,606 and 3,959,390 of the petitioner the disclosure of which is hereby incorporated by reference.

The halogen atoms of the oligomers obtained by reaction with an epihalohydrin may be replaced by a hydroxyl, thiohydroxyethyl, thiodihydroxypropyl, thioglycolate, amine, ammonium, ammonio acetate, ammonio propionate, ammonio propane sulfonate, or sulfonate grouping.

The replacement of halogen atoms by hydroxyl groupings is carried out by reaction with an alkaline salt of carboxylic acid and preferably with sodium or potassium acetate at a temperature of 150° to 200° C. in an appropriate solvent chosen advantageously from the glycols and the derivatives of glycol; the acetic ester formed is then cut by saponification by means of sodium hydroxide or potassium hydroxide or by alcoholysis by means of an inferior alcohol and preferably by means of methanol or ethanol in the presence of a basic catalyst chosen preferably from methylene or ethylate of sodium or of potassium.

The replacement of halogen atoms by a thiohydroxyethyl, thiodihydroxypropyl or thioglycolate grouping is carried out by reaction with thioethanol, thioglycerol or thioglycolate of methyl or ethyl, at a temperature of 20° to 150° C., in the presence possibly of a solvent and of an alkaline compound chosen advantageously from hydroxide, methylate and ethylate of sodium or potassium.

The replacement of halogen atoms by amine groupings is carried out as for the compounds of type I(a).

The amine functions thereby obtained may be salified or alkylated as indicated for the compounds I(b), I(c) and I(d) and transformed into ammonium, ammonio acetate, ammonio propionate or ammonio propane sulfonate function.

The hydroxyl groupings obtained may then possibly be esterified and replaced by sulfate or sulfoacetate groupings respectively by reaction with sulfuric chlorohydrin or sulfoacetic acid.

In this last case, the reaction may be carried out directly with the t-butoxy groupings.

The tensio-active cyclic polyethers of formula (I), called "Polypods" according to the invention, are present in the form of oils, pastes, waxes or powders generally soluble or dispersible in water.

They lower the surface tension of water and permit, at very weak concentrations, the solubilization of non-hydrosoluble products.

Among the non-hydrosoluble compounds which may be solubilized by the tensio-active cyclic polyethers of formula (I), it is necessary to mention dyes, perfumes, and certain pharmaceutical products.

Apart from the solubilization of these products, the tensio-active cyclic compounds of formula (I) may permit one to solubilize or to disperse mineral or polar compounds in an organic medium or hydrophobic compounds in an aqueous medium.

The compounds of the invention may be used in industry, notably in cosmetics, pharmaceutical compositions, in the textile, dyeing, insecticide and similar industries.

The invention also relates to compositions comprising at least one tensio-active cyclic polyether of formula (I).

Among these compositions, it is necessary to mention more particularly the cosmetic and pharmaceutical compositions comprising at least $0.5 \times 10^{-2}$ gram per liter or $0.5 \times 10^{-3}\%$ in weight of a tensio-active cyclic polyether of formula (I) or of a mixture of them.

The cosmetic compositions include notably the compositions designed for skin, nails, and hair care.

The compositions for hair care aim notably at shampoos and conditioners for the hair, as well as dyeing compositions and colouring shampoos.

The cosmetic compositions may be in the form of an aqueous or hydroalcoholic solution, or in the form of a cream, a gel, an emulsion or an aerosol.

The hydroalcoholic solutions include generally an alcohol or a polyol having from 1 to 4 carbon atoms and preferably ethanol or isopropanol, advantageously in a proportion of 5 to 70% of the total weight of the composition.

The cosmetic compositions for the treatment of the hair, and in particular shampoos, colouring shampoos and hair dye compositions, may also contain in addition to a tensio-active cyclic polyether of formula (I) an adjuvant chosen from the group consisting of the anionic, cationic, amphoteric, zwitterionic or non-ionic surface-active agents and their mixtures, perfumes, dyes, preservatives, foam synergists, foam stabilizers, softening agents, agents for restructuring hair, anti-dandruff agents, cosmetic resins, sequestrants, thickeners, electrolytes and cosmetic polymers.

Colouring shampoos and hair dye compositions, in addition, contain one or several direct dyes and, in particular, anthraquinionic dyes, azoic dyes, nitrated dyes of the benzene series, indophenols, indoanilines, indamines.

The pH of the compositions is generally between 3 and 11.

The invention also relates to a process for treatment of hair consisting of the application to the hair of an effective amount of an aqueous or hydroalcoholic composition including one or several tensio-active cyclic polyethers of formula (I) and possibly one or several adjuvants defined above.

The invention will be better understood with the help of the non-limiting examples which follow.

EXAMPLE 1

Preparation of mercapto-11 undecanol-1 [intermediary compound of formula (II)]

To 256 g (1.5 mole) of undecylenic alcohol, 3.7 g of azodiisobutyronitrile is added; then in the space of one hour, 105.5 g (1.5 mole) of thioacetic acid is added, while keeping the temperature between 25° and 50° C.

The product is heated to 70° C. for 4 hours, and one obtains the compound:

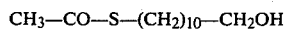

The rate of reaction determined by titration of the SH grouping is 95%.

The reactive mass is mixed with 200 ml of ethanol at 96° C. and 40 ml of water. The mass is saponified by adding 165 g of aqueous solution of sodium hydroxide at 10 meq/g (milliequivalent per gram) and heating for 1 hour at the temperature of reflux. The product is acidified with chlorohydric acid and the organic phase is separated by decantation and washed three times with 300 ml of water at 80° to 90° C.

After dehydration, the mercapto-11 undecanol-1 is distilled at 126° to 130° C. under pressure of 0.4 mm of Hg.

The product obtained is in the form of a white solid having a SH index of 4.8 meq/g.

EXAMPLE 2

Preparation of the mercapto-11 undecanoic-1 acid [intermediary compound of formula (III)]

To 184 g (1 mole) of undecylenic acid, 2.5 g of azodiisobutyronitrile is added; then in 40 minutes, 76 g (1 mole) of thioacetic acid is added. The reaction is exothermic and the temperature rises from 24° to 65° C. The product is heated to 70° C. for 3 hours. The compound of the following formula is obtained:

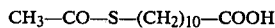

The rate of reaction according to titration of the —SH grouping is 98–99%.

The reactive mass is diluted with 100 g of ethanol at 96° C. Then 220 g (2.2 moles) of aqueous solution of sodium hydroxide at 10 meq/g is added over 30 minutes. After being heated for 1 hour at 70° C., the product is acidified with 190 ml of concentrated hydrochloric acid.

The mercapto-11 undecanoic-1 acid is decanted and then washed four times with 100 ml of water at 65° to 70° C. It is then dried by heating under reduced pressure and distilled at 145° C. under a pressure of 0.07 mm Hg.

Acid index=4.38 meq/g.
SH index=4.28 meq/g.

EXAMPLE 3

Preparation of the tetramer of epichlorohydrin [intermediary compound of formula (IV)] by polymerization of epichlorohydrin

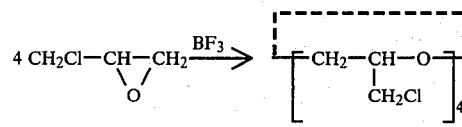

In a reactor of 6l, 1180 g of epichlorohydrin and 500 ml of carbon tetrachloride are mixed. The mixture is chilled to 10° C. by immersion in an ice bath. Under energic agitation, 16 g of etherate of trifluoride of boron in solution in 1 liter of carbon tetrachloride is added in 6 hours. One keeps the temperature during this time between 10° and 13° C.

The temperature is allowed to rise and the mixture is progressively carried to the temperature of reflux during 1 hour. 50 g of dry and finely pulverized sodium carbonate is added and agitated for 2 hours at reflux. The mineral salts are then separated by filtration. The carbon tetrachloride is evaporated under reduced pressure, then one fractionates by distillation.

Thus, there is obtained, at 185° C. and under pressure of 0.2 mm of Hg, 210 g of product which is present in the form of a colorless vitreous mass crystalizing at the end of several days. Titration of organic chlorine: 10.6 meq/g.

EXAMPLE 4

Preparation of intermediary compound of formula (V)

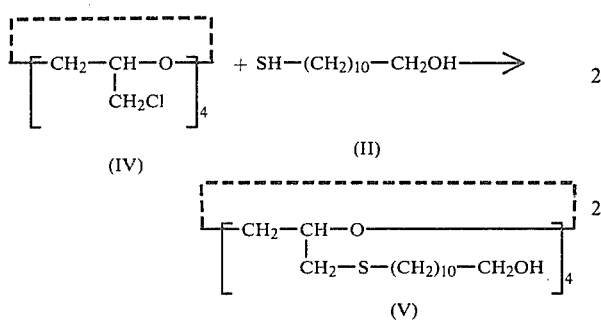

74 g (0.8 equivalent in chlorine) of epichlorohydrin tetramer and 167 g (0.8 mole) of compound of formula (II) are dissolved in 600 ml of absolute ethanol. 152 g (0.82 mole) of sodium methylate in methanol, at 5.4 meq/g is added drop by drop at 40° C. in 30 minutes.

After 7 hours of heating at reflux, the rate of reaction is 96%.

The residual alkalinity is possibly neutralized with concentrated HCl. Then the sodium chloride formed is separated by filtration.

After elimination of ethanol by distillation, a solid compound whose index of thioether is 3.75 meq/g and the index of hydroxyl is 4.1 meq/g is obtained.

EXAMPLE 5

Preparation of the intermediary compound

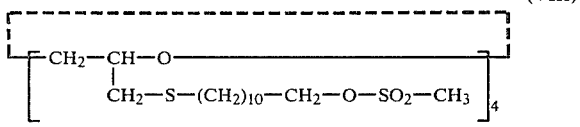

(VIII)

[sulfonic methane ester of compound (V) prepared in Example 4]

180 g of compound (V), (0.7 theoretical equivalent in hydroxyl grouping) is dissolved in 300 ml of anhydrous benzene. 71.5 g of triethylamine (0.7 mole) is added and then, at the temperature of 15° C. and in 30 minutes, 80 g (0.7 mole) of methane sulfochloride is added. The product is maintained under agitation for 2 hours between 15° and 20° C.

The triethylamine chlorohydrate is filtered and washed twice with 200 ml of benzene.

The benzenic phase is extracted with water and then dried on sodium sulfate.

After elimination of the solvent, the compound of formula (VIII) is obtained in the form of a clear yellow oil whose index of saponification is 3.08 meq/g.

EXAMPLE 6

Preparation of the intermediary compound

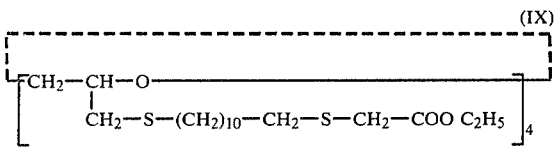

To 34 g (100 meq) of intermediary compound of formula (VIII), prepared according to Example 5, dispersed in 100 g of absolute ethanol, 12.3 g (0.1 mole) of ethyl thioglycolate and 18.6 g (0.1 mole) of sodium methylate in methanol, at 5.4 meq/g are added (at the surrounding temperature).

The solution is heated for 7 hours at reflux. The methane sodium sulfonate formed thereby is filtered. The solvent is eliminated under reduced pressure.

The compound of formula (IX) in the form of a clear brown oil is obtained which has the following characteristics:

Index of saponification: 2.7 meq/g.
S%: 17.7.

EXAMPLE 7

Preparation of a compound of formula (I) in which A refers to the grouping:

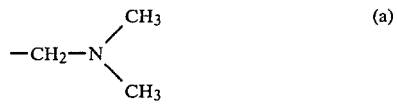

43 g (0.13 equivalent) of intermediary compound of formula (VIII), prepared in Example 5 is dissolved in 150 g of benzene, 120 ml of benzenic solution of dimethylamine at 33% is added in 20 minutes and at ordinary temperature.

After 5 hours of agitation at 40° C., the reaction rate calculated according to the acid index appearing is practically quantitative.

The excess amine and the solvent are eliminated under reduced pressure, after neutralization of the methane sulfonic acid formed thereby, with sodium methylate. The reactive mass is dissolved in 250 ml of chloroform and extracted three times with 60 ml of water.

After drying, a clear brown oil containing 11.5% of S and 4.74% of nitrogen is obtained.

This oil is soluble in water after neutralization with an acid, for example, lactic acid or chlorohydric acid.

EXAMPLE 8

Preparation of a compound of formula (I) in which A refers to the grouping:

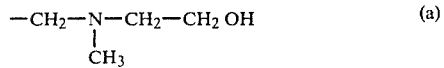

To 33.8 g (100 meq) of intermediary compound of formula (VIII) prepared according to Example 5, 16 g (0.2 mole) of methylethanolamine is added at 45° C. and in 10 minutes. After 8 to 9 hours at 80° C., the reaction is practically quantitative.

The reactive mass is taken up with 100 ml of isopropanol and 16.3 g of sodium methylate in methanol, at 5.4 meq/g is added. The sodium methane sulfonate is filtered out and the solvent and the excess amine are eliminated by distillation under reduced pressure.

The residue is taken up in chloroform and the organic phase is washed in water.

A clear brown thick oil soluble in a diluted acid medium and having the following characteristics is obtained:

S% = 10.1.
N% = 4.42.

EXAMPLE 9

Preparation of a compound of formula (I) in which A refers to the grouping:

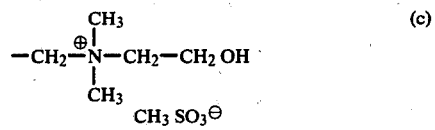

To 13.5 g (40 meq) of intermediary compound of formula (VIII) prepared according to Example 5, 3.63 g (0.04 mole) of dimethyl ethanolamine is added and heated for 3 hours at 60° C.

A clear yellow paste soluble in water is obtained.
S% = 15.63–15.89.

EXAMPLE 10

Preparation of a compound of formula (I) in which A refers to the grouping:

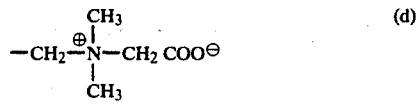

To 5.75 g (0.020 equivalent of amine) of compound prepared according to Example 7, 2.45 g (0.020 mole) of chloracetate of ethyl is added at ordinary temperature.

The product is heated for 1 hour at 50° C.

The rate of reaction, calculated according to the index of remaining basicity, is practically quantitative.

20 ml of ethanol is added to the reactive medium; then 20 meq of NaOH in solution in 10 ml of water is added. After 35 minutes of heating to reflux, the product is neutralized by addition of 2 ml of concentrated hydrochloric acid.

After elimination of sodium chloride and solvents, the product is taken up with 20 ml of dimethylether of diethyleneglycol.

A white powder soluble in water, having a melting point of 150° C. and containing 3.2% nitrogen and 8.6% sulfur is thereby obtained.

EXAMPLE 11

Preparation of a compound of formula (I) in which A refers to the grouping:

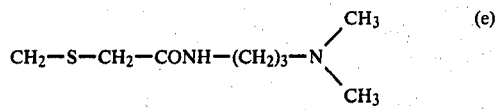

To 5.5 g (15.2 meq) of intermediary compound of formula (IX), prepared according to Example 6, 0.1 g (0.5 meq) of sodium methylate in methanol and 3.5 g (30 meq) of dimethyl aminopropylamine are added.

The reactive medium is heated for 15 hours at 110° C.

The reactive mass is dissolved in 20 ml of chloroform and washed three times with 10 ml of water. The organic phase is then dried on sodium sulfate, then heated under reduced pressure to eliminate the ethanol thereby formed and the methanol used as a solvent.

The desired compound is in the form of a paste of clear brown color, soluble in water in the presence of an acid, for example, hydrochloric or lactic acid.

The compound obtained possesses the following characteristics:

Index of basicity: 2.5 meq/g.
N%: 15.14.
S%: 6.57.

EXAMPLE 12

Preparation of a compound of formula (I) in which A refers to the grouping:

—COOH   (g)

In 600 g of absolute ethanol, 22.3 g (0.24 equivalent in chlorine) of epichlorohydrin tetramer and 55.2 g (0.24 mole) of mercapto-11 undecanoic-1 acid are dissolved. Then, in 45 minutes, 96 g (0.48 mole) of sodium methylate in methanol is added. The reactive mass is heated for 5 hours at 50° C., and then 3 hours to reflux.

The product is acidified by the addition of concentrated hydrochloric acid. The acidified product is diluted with warm water. The organic phase is separated by decantation at 80° C., and washed and dried under reduced pressure.

Thus, there is obtained the desired compound in the form of a white solid with a melting point of 60° C., acid index 3.49 meq/g, and which is soluble in water, in the form of an alkaline salt or an amine salt, for example, sodium salt, potassium or triethanolamine salt.

EXAMPLE 13

Preparation of a compound of formula (I) in which A refers to the grouping:

—CH₂—S—CH₂—COOH   (g)

To 18.1 g (0.05 equivalent) of compound of formula (IX) prepared in Example 6, dissolved in 200 ml of ethanol at 96° C., 6 g of aqueous solution of NaOH at 10 meq/g and 20 ml of water are added. The mixture is heated for 1 hour to reflux.

200 ml of water is added. After acidification with HCl, the corresponding acid is extracted with chloroform.

After drying under reduced pressure, the desired compound is obtained in the form of a clear yellow solid, soluble in water, in the form of an alkaline salt or an amine salt, for example in the form of sodium salt, potassium salt, or triethanolamine salt.

The characteristics of this compound are as follows:
Acid index: 2.7 meq/g.
S%: 19.1.

EXAMPLE 14

Preparation of a compound of formula (I) in which A refers to the grouping:

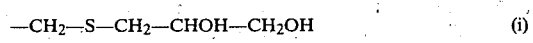  (i)

To 17 g (50 meq) of intermediary compound of formula (VIII), prepared according to Example 5, dispersed in 20 g of absolute ethanol, 6 g (0.050 mole) of thioglycerol in 10 g of absolute ethanol is added. 13.5 g of sodium methylate in methanol, at 3.7 meq/g is then added.

The reaction mass is heated to reflux during 7 hours.

The methane sodium sulfonate thereby formed is separated by filtration and the solvent is eliminated under reduced pressure.

The desired compound so obtained possesses the following characteristics:
OH index: 5.8 meq/g.
S%: 17.5.

EXAMPLE 15

Preparation of a compound of formula (I) in which A refers to the grouping:

  (i)

To 7 g (0.020 equivalent in hydroxyl grouping) of compound prepared according to Example 14, 0.35 g of sodium methylate is added; then, in the space of 1 hour, at a temperature of 150° C., 7.65 g (0.1 mole) of glycidol is added.

The desired compound thus obtained is in the form of a clear brown paste soluble in water.

Cloud point in salted water containing 25 weight percent NaCl: 88° C.

EXAMPLE 16

Preparation of a compound of formula (I) in which A refers to the grouping:

  (h)

where M refers to H or NH₄ or HN(CH₂—CH₂OH)₃.

(a) Preparation of the acid (M=H)

5.2 g (0.02 equivalent in hydroxyl grouping) of intermediary compound of formula (V) are put into solution in 10 ml of chloroform. In the space of 10 minutes, 2.33 g of sulfuric chlorohydrin in solution in 5 ml of chloroform is added. The temperature rises from 20° to 30° C.; agitation is maintained for 20 minutes.

After elimination of the chloroform under reduced pressure, a clear yellow oil is obtained.

(b) Preparation of ammonium salt (M=NH₄)

The acid thereby obtained is put into solution in 10 ml of ethanol at 90° C. Under agitation 6 ml of 6 N ammoniac is added. After concentration, the reaction mass is taken up with 2 ml of absolute ethanol and 10 ml of ether; then the ammonium salt is succion filtered then washed with 5 ml of ether. It is in the form of a white powder soluble in warm water. By recooling, the aqueous solution gels to form a translucid mass.

(c) Preparation of triethanolamine salt [M=HN(CH₂—CH₂OH)₃]

To the acid put in solution in 10 ml of ethanol at 90° C., 3 g of triethanolamine in solution in 10 ml of ethanol at 90° C. is added. The solvent is eliminated by distillation under reduced pressure. The product is in the form of a clear yellow paste, soluble in warm water, giving an opalescence when cool.

EXAMPLE 17

Preparation of a mixture of compounds of formula (I) in which A refers to the grouping:

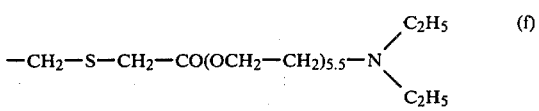  (f)

[grouping of type (f) in which w=1 and n=5.5]

18.07 g (0.05 equivalent in ester grouping) of intermediary product of formula (IX) are mixed with 17.3 g of oxyethylenated N,N-diethylamino ethanol (0.05 mole).

Under agitation, 1 g of sodium methylate in methanolic solution at 30% is added. The temperature is raised to 110° C. while eliminating the ethanol at ordinary pressure, then under reduced pressure for 1 hour 30 minutes.

The product thereby obtained is in the form of a brown oil, very dispersible in water, soluble in acetic acid or in diluted lactic acid.

Basicity index: 1.6 meq/g.

EXAMPLE 18

Preparation of the mixture of compounds of formula (I) in which A refers to the grouping:

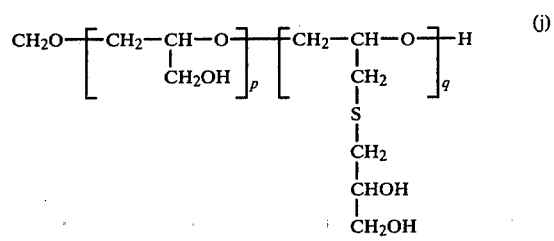  (j)

To 13 g (0.05 equivalent in hydroxyl grouping) of intermediary compound of formula (V) melted, 0.1 ml of BF₃ complex in ether and 1 g of dry zinc chloride are added. The mixture of 13 g of tertiobutylglycidylether (0.1 mole) and 9.25 g of epichlorohydri (0.1 mole) is introduced under agitation for 20 minutes. It is heated for 8 hours at 105° C. under agitation. Then, 0.25 g of sulfoacetic acid is added and the mixture is heated at 100° C. under agitation until the end of gaseous release. Duration of the reaction: about 8 hours.

The reactive mass is taken up again with 40 ml of dichloroethane and the solution is washed with 40 ml of water saturated with sodium bicarbonate, then with 40 ml of water. The organic phase is dried on anhydrous sodium sulfate and concentrated dry.

15.1 g of the so-obtained product is put in solution in 50 ml of absolute ethanol. 6.95 g of thioglycerol is added, the mixture being heated at 45° C.

Under agitation, 9.5 g of methanolic solution of sodium methylate at 6.1 meq/g is added.

The reactive medium is maintained for 8 hours at reflux. The reaction is followed by titration of the mercaptan function. The sodium chloride thereby formed is separated by filtration and the filtrate concentrated dry under reduced pressure.

One obtains a thick brown oil, dispersible in water.

Cloud point measured at a concentration of 5% in an aqueous solution containing 25% butyldiglycol at 79° C.

EXAMPLE 19

The following coloring lotion is prepared:
Compound of Example 14: 1 g
1-[N(3-amino propyl)amino]anthraquinone: 0.05 g
Water q.s.p.: 100 g This solution, applied during 30 minutes on bleached hair, gives them, after rinsing, shampooing and rinsing, a clear rose salmon tint.

EXAMPLE 20

The following coloring lotion is prepared:
Compound of Example 9: 1.2 g
4-[N-(beta-hydroxy ethyl)]amino phenyl azo-4-nitro phenyl: 0.1 g
Water q.s.p.: 100 g This solution, applied during 30 minutes on bleached hair, gives them, after rinsing, shampooing and rinsing, a golden sable tint.

EXAMPLE 21

The following coloring lotion is prepared:
Salt of triethanolamine of the compound of Example 13: 1 g
1,4-bis-(methylamino)-2-nitro phenyl: 0.08 g
Water q.s.p.: 100 g This lotion, applied during 30 minutes on bleached hair, gives them, after rinsing, shampooing and rinsing, a clear rose cyclamen tint.

EXAMPLE 22

An anionic shampoo of the following composition is prepared:
Compound of Example 7: 0.6 g
Lauryl triethanolamine sulfate: 6 g
Lauric diethanolamide: 3 g
Lactic acid q.s.p.: pH 6
Water q.s.p.: 100 g

EXAMPLE 23

A non-ionic shampoo of the following composition is prepared:
Compound of Example 8: 0.8 g
Hydroxy alkyl ether of polyglycerol of the formula:

where R represents a mixture of alkyl radicals having from 9 to 12 carbon atoms: 9 g
Lactic acid q.s.p.: pH 6.7
Water q.s.p.: 100 g The solutions of Examples 22 or 23 are applied to a head of hair in order to soften all the soiled areas. The hair is rinsed and subjected to a second application; a rich lather is obtained and then rinsed. The dried hair separates easily and permits easy shaping or setting of the hair.

What is claimed is:

1. Tensio-active cyclic polyethers of the general formula:

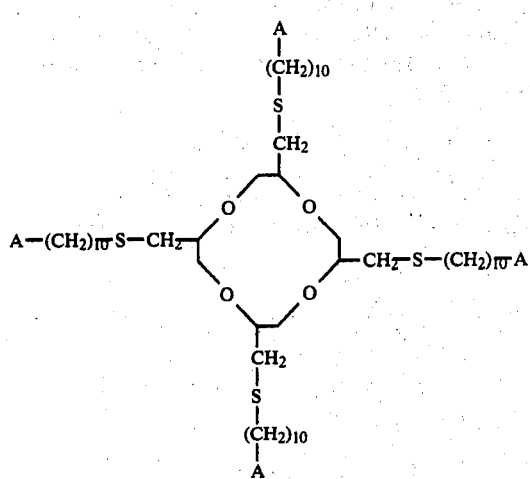

wherein A refers to a cationic, anionic, zwitterionic or non-ionic hydrophile block which includes one or more groupings, identical or different, selected from the group consisting of amine, ammonium, ammonio alkyl carboxylate, ammonio alkyl sulfonate, carboxylic amide, ether, thioether, hydroxyl, carboxylic ester and carboxylic acid groupings.

2. Tensio-active cyclic polyether according to claim 1, wherein the hydrophile block A is selected from the group consisting of:

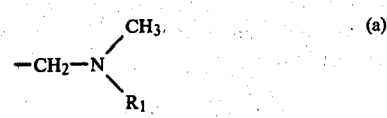

where $R_1$ refers to $CH_3$ or $+CH_2-CH_2-O+_{\overline{n}}H$ and n refers to a whole or decimal number from 1 to 10;

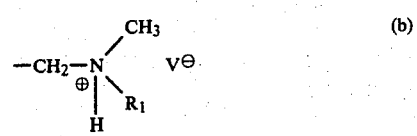

where $V^\ominus$ refers to an anion of an organic or mineral acid and $R_1$ has the meaning shown in (a);

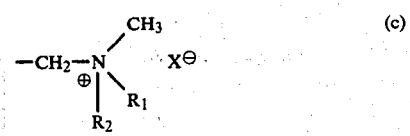

where $R_2$ refers to an alkyl or hydroxyalkyl radical having from 1 to 3 carbon atoms, $X^\ominus$ refers to an anion, and $R_1$ has the meaning shown in (a);

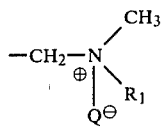

where $Q^\ominus$ refers to a member selected from the group consisting of $-CH_2-COO^\ominus$, $-CH_2-CH_2-COO^\ominus$, and $CH_2-CH_2-CH_2-SO_3^\ominus$, and $R_1$ has the meaning shown in (a);

$$-(CH_2-S-CH_2)_w-CONH-(CH_2)_m-B \quad (e)$$

where m refers to 2 or 3, w refers to the number 0 or 1, B refers to a member selected from the group consisting of:

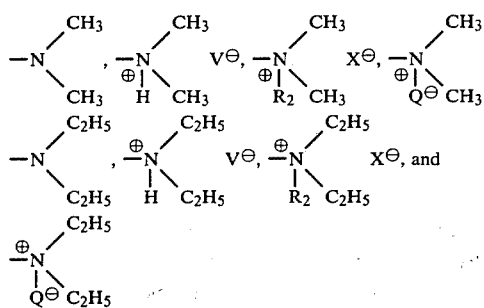

in which $V^\ominus$ has the meaning shown in (b), $R_2$ and $X^\ominus$ have the meaning shown in (c), and $Q^\ominus$ has the meaning shown in (d);

$$-(CH_2-S-CH_2)_w-\underset{\underset{O}{\|}}{C}-(O-CH_2-CH_2)_n-B \quad (f)$$

where w refers to the number 0 or 1, n refers to a whole or decimal number from 1 to 10, and B has the meaning shown in (e);

$$-[CH_2-S-CH_2]_w-COOM_1 \quad (g)$$

where w refers to the number 0 or 1, and $M_1$ refers to ammonium or an alkali metal;

$$-CH_2-O-SO_3M \quad (h)$$

where M refers to a hydrogen atom, ammonium or an alkali metal;

$$-[CH_2-S-Y-O]_nH \quad (i)$$

where n refers to a whole or decimal number from 1 to 10, and Y refers to an ethylene or hydroxypropylene radical; and

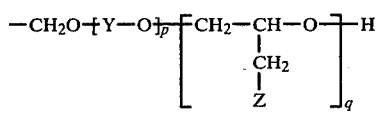

where p and q, identical or different, refer to a whole or decimal number from 0 to 10 with the proviso that p and q do not simultaneously refer to zero, Y has the meaning shown in (i), Z refers to a member selected from the group consisting of:

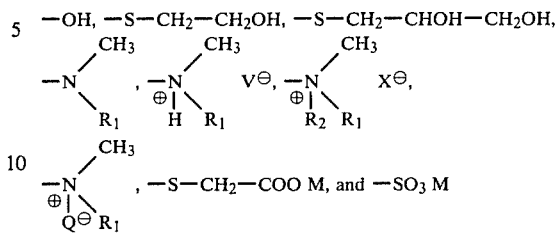

and, in addition, when p refers to zero or when Y refers to ethylene, Z may refer to $-O-SO_3-M$ or $-O-CO-CH_2-SO_3M$, in these groupings $R_1$ refers to $CH_3$ or $-[CH_2-CH_2-O]_nH$, n refers to a whole or decimal number from 1 to 10, $V^\ominus$ refers to an anion of an organic or mineral acid, $R_2$ refers to a methyl, hydroxyethyl or dihydroxypropyl radical, $X^\ominus$ refers to an anion, $Q^\ominus$ refers to $-CH_2-COO^\ominus$, $-CH_2-CH_2-COO^\ominus$ or $-CH_2-CH_2-CH_2-SO_3^\ominus$ and M refers to a hydrogen atom, ammonium or an alkali metal.

3. Intermediary compounds for the preparation of compounds of formula (I) in claim 1 having the formula:

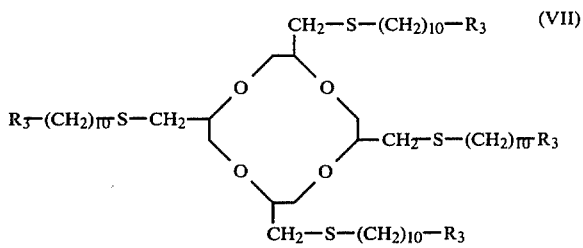

where $R_3$ refers to $-CH_2OH$; $-CH_2-O-SO_2-CH_3$; $-CH_2-O-SO_2-C_6H_4-CH_3$; $-COOH$; $-COOCH_3$; $-COOC_2H_5$; $-CH_2-S-CH_2-COOH$; $-CH_2-S-CH_2-COOCH_3$ or $-CH_2-S-CH_2-COOC_2H_5$.

4. Tensio-active cyclic polyether according to claim 2, wherein the hydrophile block A is the grouping (a).

5. Tensio-active cyclic polyether according to claim 2, wherein the hydrophile block A is the grouping (b).

6. Tensio-active cyclic polyether according to claim 2, wherein the hydrophile block A is the grouping (c).

7. Tensio-active cyclic polyether according to claim 2, wherein the hydrophile block A is the grouping (d).

8. Tensio-active cyclic polyether according to claim 2, wherein the hydrophile block A is the grouping (e).

9. Tensio-active cyclic polyether according to claim 2, wherein the hydrophile block A is the grouping (f).

10. Tensio-active cyclic polyether according to claim 2, wherein the hydrophile block A is the grouping (g).

11. Tensio-active cyclic polyether according to claim 2, wherein the hydrophile block A is the grouping (h).

12. Tensio-active cyclic polyether according to claim 2, wherein the hydrophile block A is the grouping (i).

13. Tensio-active cyclic polyether according to claim 2, wherein the hydrophile block A is the grouping (j).

14. Tensio-active cyclic polyether according to claim 2, wherein the hydrophile block A is the grouping

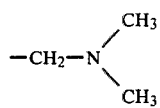

15. Tensio-active cyclic polyether according to claim 2, wherein the hydrophile block A is the grouping

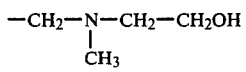

16. Tensio-active cyclic polyether according to claim 2, wherein the hydrophile block A is the grouping

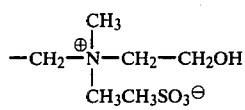

17. Tensio-active cyclic polyether according to claim 2, wherein the hydrophile block A is the grouping

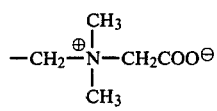

18. Tensio-active cyclic polyether according to claim 2, wherein the hydrophile block A is the grouping

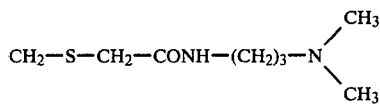

19. Tensio-active cyclic polyether according to claim 2, wherein the hydrophile block A is the grouping

—COOH.

20. Tensio-active cyclic polyether according to claim 2, wherein the hydrophile block A is the grouping

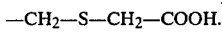

—$CH_2$—S—$CH_2$—COOH.

21. Tensio-active cyclic polyether according to claim 2, wherein the hydrophile block A is the grouping

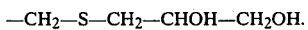

—$CH_2$—S—$CH_2$—CHOH—$CH_2OH$.

22. Tensio-active cyclic polyether according to claim 2, wherein the hydrophile block A is the grouping

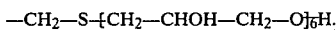

—$CH_2$—S—$[CH_2$—CHOH—$CH_2$—O$]_6$H.

23. Tensio-active cyclic polyether according to claim 2, wherein the hydrophile block A is the grouping

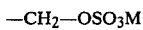

—$CH_2$—$OSO_3M$ where M is H, $NH_4$ or $NH(CH_2$—$CH_2OH)_3$.

24. Tensio-active cyclic polyether according to claim 2, wherein the hydrophile block A is the grouping

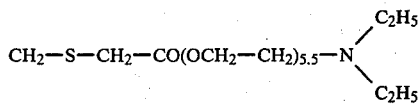

25. Tensio-active cyclic polyether according to claim 2, wherein the hydrophile block A is the grouping

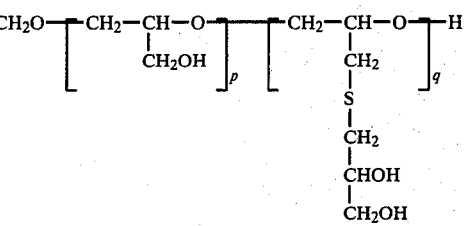

where p=q=2.

26. Intermediary compound according to claim 3, wherein $R_3$ is $CH_2OH$.

27. Intermediary compound according to claim 3, wherein $R_3$ is —$CH_2$—O—$SO_2$—$CH_3$.

28. Intermediary compound according to claim 3, wherein $R_3$ is —$CH_2$—S—$CH_2$—$COOC_2H_5$.

* * * * *